US008371999B2

(12) United States Patent
DeAlva

(10) Patent No.: US 8,371,999 B2
(45) Date of Patent: Feb. 12, 2013

(54) SEXUAL AID SYSTEM

(76) Inventor: John DeAlva, Chula Vista, CA (US)

( * ) Notice: Subject to any disclaimer, the term of this patent is extended or adjusted under 35 U.S.C. 154(b) by 627 days.

(21) Appl. No.: 12/564,013

(22) Filed: Sep. 21, 2009

(65) Prior Publication Data

US 2010/0076257 A1 Mar. 25, 2010

Related U.S. Application Data

(60) Provisional application No. 61/098,572, filed on Sep. 19, 2008.

(51) Int. Cl.
*A61F 5/00* (2006.01)

(52) U.S. Cl. ........................................................ 600/38

(58) Field of Classification Search .................. 128/897, 128/898; 600/38–41

See application file for complete search history.

(56) References Cited

U.S. PATENT DOCUMENTS 3,996,930 A * 12/1976 Sekulich ........................ 601/137
5,690,603 A * 11/1997 Kain ................................ 600/38
6,132,366 A * 10/2000 Ritchie et al. ................... 600/38
D605,779 S * 12/2009 Murison ...................... D24/215
2004/0230093 A1* 11/2004 Marshall ......................... 600/38

* cited by examiner

*Primary Examiner* — Samuel Gilbert
(74) *Attorney, Agent, or Firm* — Donn K. Harms

(57) ABSTRACT

A sexual aid device formed of a substantially U-shaped, member having a proximal end adapted for engagement within the vagina of a user distal end positioned to oppose the proximal end in a biased engagement with intra vaginal and external sexually sensitive surfaces of the user's body. A skeletal member running axially within said U-shaped member may be employed to vary the force of the biased engagement and reshape the U-shaped member. A projecting elongated member adjacent to the distal end of the U-shaped member is engageable by the user or body contact with a second user to impart force to the U-shaped member for sexual stimulation.

15 Claims, 5 Drawing Sheets

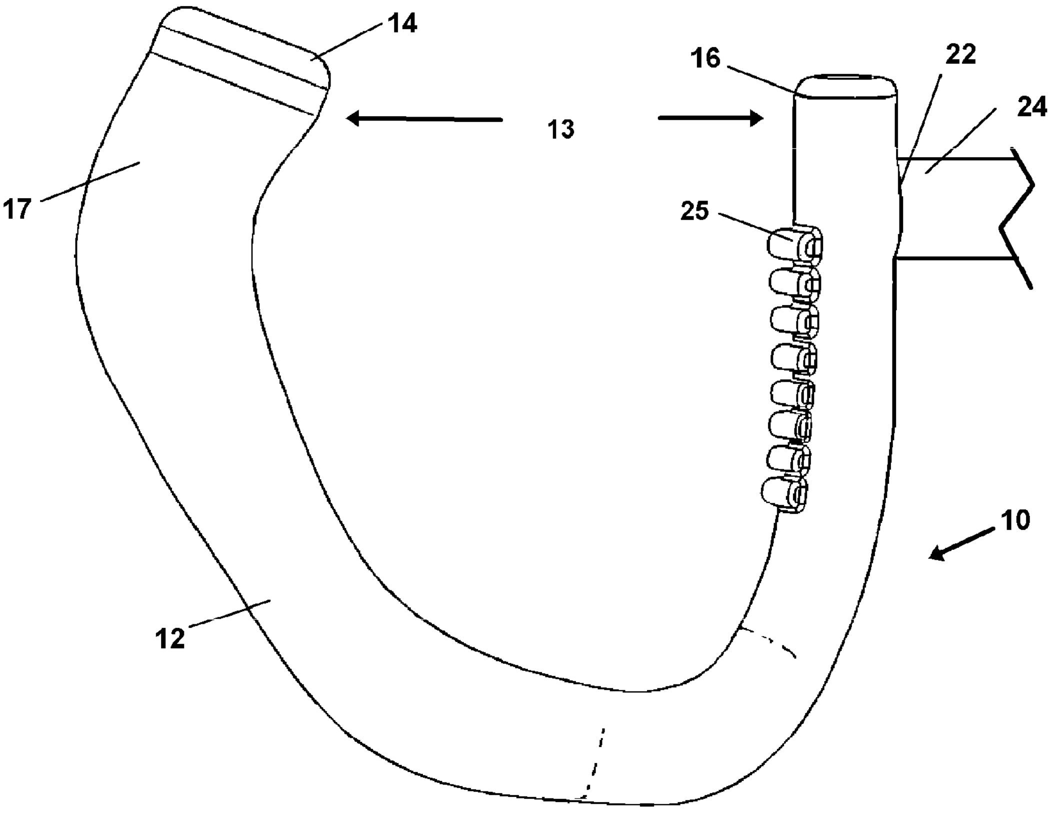
Fig, 1
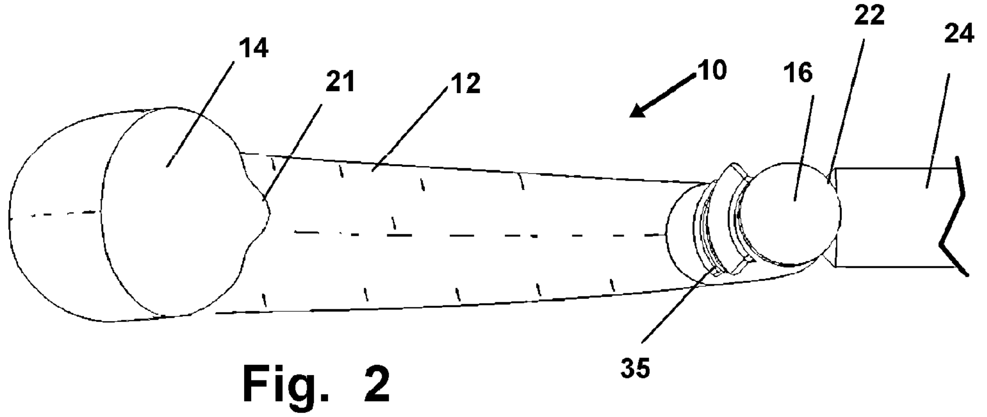
Fig. 2

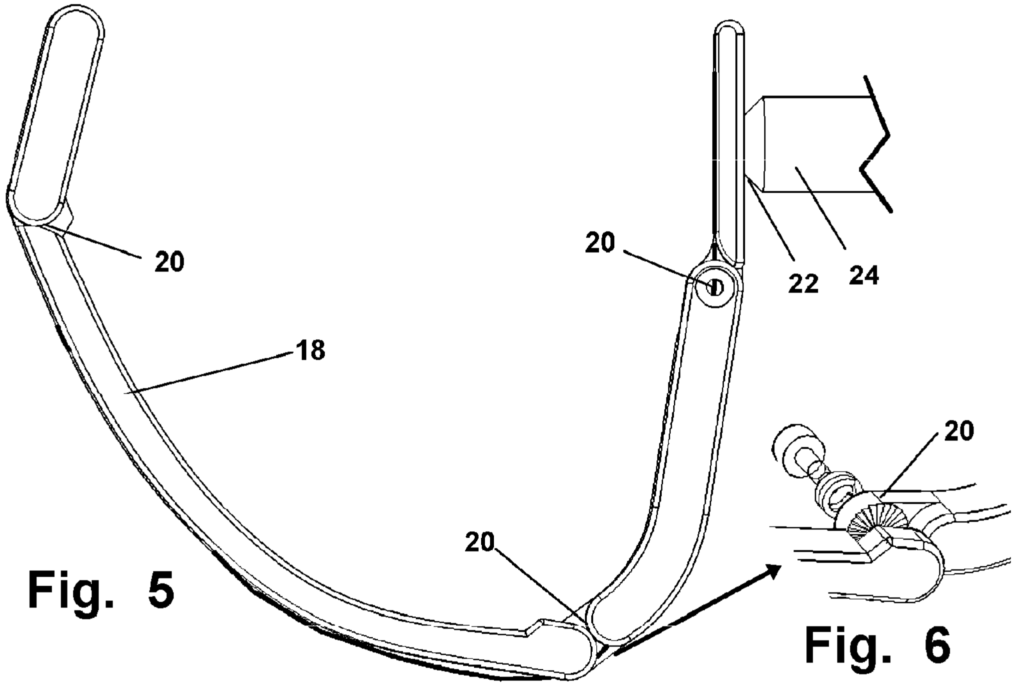
Fig. 5
Fig. 6
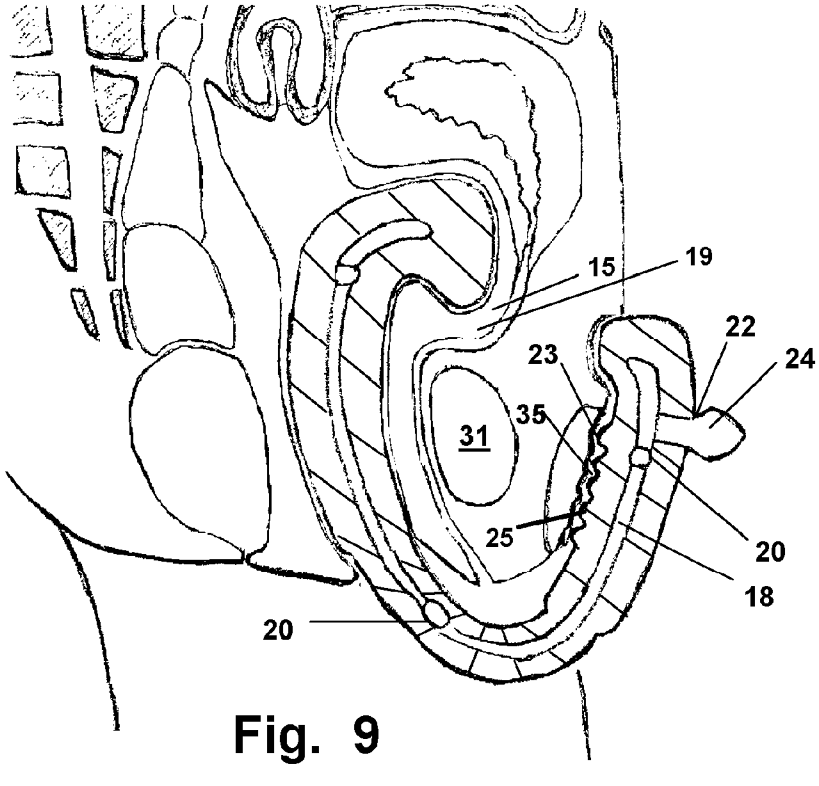
Fig. 9

SEXUAL AID SYSTEM

This application claims priority to U.S. Provisional Patent Application No. 61/098,572 filed on Sep. 19, 2008 and respectively incorporated herein in it's entirety by reference.

BACKGROUND OF THE INVENTION

1. Field of the Invention

The present invention relates to articles which are adapted to enhance sexual function and user pleasure. More specifically, the device relates to a sexual stimulation device which is retainable upon the female wearer without the aid of straps and belts and which may be adapted for concurrent use between two sexual partners or simply employed by a single user. The device is dimensioned in a manner to sexually stimulate intra vaginal and external erotic arousal areas of users.

2. Prior Art

Sexual aids for increasing and inducing sexual pleasure have been known and employed in different cultures for hundreds of years. Such devices have been provided primarily with self-stimulation of the user in mind and therefor adapted for use by only one person.

Modernly, sexual aids have been developed which may be employed by one user or two parties during sexual intercourse between them. In the case of two females, conventionally such devices are generally a phallic shaped member which extends from a base engaged on one female and is employed to penetrate her partner. Such devices however employ straps and belts and other inconvenient components to remain mounted on the one female while being employed upon the other. They are as such, uncomfortable and inconvenient.

Further, these belt-engaged devices are generally not designed nor adapted to provide sexual stimulation to either individually or to both parties during their physical engagement. Thus, the sexual satisfaction of the party wearing the device, or in many cases on the receiving end of the device, can be severely lacking. Most conventional two-person devices employ a member to penetrate and provide sexual pleasure to one of the user's while in some fashion concurrently stimulating the wearer.

Variations of this type of device do include a dual ended phallic shaped member intended to be engaged within both females concurrently. However, since the device is mounted to neither partner, use to physically stimulate both parties concurrently requires some rather gymnastic maneuvers by both, and excellent timing in order not to cause a premature dismount from the device by either user.

Neither type of these sexual aids is adapted to be self-retained in either partner during a sexual encounter. Without the aid of straps and belts and mounts, or well-coordinated timing during employment of unmounted devices by both parties, disengagement and frustration will generally prevail.

As such, there is an unmet need for a sexual aid device that is adapted for self-retention on at least one user during a mutual or individual sexual encounter. When employed with another partner, such a device should provide mutual simultaneous pleasurable feelings induced by the movement of both parties engaged with the device. Such a device should be adapted at a first end to provide intra vaginal and external sexual stimulation to the wearer singularly or when used with a partner. Such a device should be adapted through an engageable component, to provide concurrent intra vaginal and external stimulation to the other party during sexual encounter with the wearer.

SUMMARY OF THE INVENTION

The sexual stimulation device herein disclosed and described provides a unique solution to the noted shortcomings of the prior art. The device is self-retained without the aid of straps or belts or other means to maintain the device engaged physically with the user or wearer.

When employed with a female wearer, the device in one preferred mode, is adapted for the wearer to self-retain the curved elongated member in a mounted fashion upon the user's body in a position adapted to provided sexual stimulation during use. This engagement is maintained without the aid of belts or straps, instead employing a means to bias the distal ends of the curved member toward each other and maintain a pressured clamping or engagement upon the intra vaginal and external body portions of the user. The device employing a generally U-shaped member, when employed by a female user, has a proximal end for intra vaginal engagement within the wearing user.

At a distal end opposite the proximal end, the device in one preferred mode provides an engagement point connector positioned adjacent to the distal end. This connector at an engagement point is adapted for engagement of a phallic shaped elongated member, which engaged adjacent to the distal end of the device will extend perpendicular therefrom for a distance.

The elongated member so engaged serves two purposes in that it allows a user, in a solo employment of the device, to grip it and use their hand force to move the elongated member and the engaged curved member in different directions. This movement provides a means to increase intra vaginal and external stimulation of the wearer's erogenous zones.

When the device is employed between two parties, the elongated member extending from the user-engaged curved member, may be employed to stimulate external erogenous areas of the partner. It may also be used to penetrate the wearer's sexual partner and provide intra vaginal sexual stimulation. This stimulation is enhanced by movement of the wearer and partner movements during joint use.

During joint use, physical contact of the member extending from the distal end of the device with a partner, will also produce force upon the curved member which serves to act upon the vaginally engaged proximal end to produce vibration, friction, and pressure upon the self-retained females own Grafenberg Spot or G-spot intra vaginally. This movement and force induced to the member by the concurrent engagement with the user and the sexual partner also acts to provide manual stimulation to the clitoris of the wearer having the device vaginally engaged at the proximal end. This stimulation to the wearer is constant during enjoyment with their partner and natural movements therebetween, and provides additional stimulation during normal sexual movements without the need for mechanical devices such as vibrators. This is because forces from the elongated member inducted by the partner are communicated to and act upon the U-shaped member.

The distal end of the U-shaped member is preferably dimensioned to position it partially against the lower abdomen of the female wearing the device. In the simplest mode of the device, wherein the U-shaped member is formed of resilient material such as silicone or polyethylene, a natural bias occurs of the distal end toward the proximal end once the two ends are pulled apart slightly from their neutral position. This bias serves to induce a clamping force of the device with pressure being communicated intra vaginally and externally to the wearer in two particularly sexually stimulating positions of their body.

In another preferred mode of the device the U-shaped member has an internal skeletal structure extending coaxially through most of the length of the body of the U-shaped member. The skeletal structure is covered by a surrounding resilient and flexible synthetic material such as silicone to thereby form the U-shaped member exterior portion.

In this mode of the device the internal skeletal structure is formed of material sufficiently resilient to provide an increase in the biasing of the proximal and distal ends toward each other. This biasing is a most important aspect of the device for self-retention without straps, and in order for it to provide direct contact of the proximal end with, and stimulation to the G-spot and the inside surface at the distal end with the clitoris. Clitoral stimulation is well known to be sexually stimulating and the G-spot is a nerve reflex area inside the vagina, along the anterior surface know to provide powerful sexual sensations to a female when properly stimulated. The biasing of the two ends of the U-shaped member produced a clamping effect and increased contact force with both sexually stimulating body parts of the female user.

The coaxial skeletal component may be a flexible material such as silicone or polyethylene of a harder durometer, and therefor stiffer than the external portion surrounding the coaxial skeletal component. Or, it may be formed of stiffer material such as fiberglass, spring steel or stainless steel positioned along the center axis of the U-shaped member for a substantial portion of its length. Formed in this fashion, U-shaped member upon a movement of the distal and proximal ends away from each other, will resist such movement with greater inward force than if the entire U-shaped member were formed of one type of silicone or resilient material as in the first mode of the device. Thus, the user gains an increase in the force of the surface contact of the external surface of the U-shaped members with intra vaginal and external sexual stimulation areas of their body.

Additionally preferred in an enhanced mode of the device is a means for user-configuring of the shape of the U-shaped member to increase sexual stimulation. In this mode, a plurality of malleable or bendable points are provided along the coaxial positioned skeletal structure. This allows the user a means to bend or articulate the skeletal component and thereby the surrounding skin of the device and thereby allow for exact positioning of the proximal end upon the G-spot. The user-configurable skeletal component also provides a means to adjust the width of separation of the distal and proximal ends and the biasing force of both ends of U-shaped member towards each other. In this fashion, the user is afforded a means to achieve a better biased contact of the proximal end with the G-spot and the distal end against the lower abdominal wall and clitoral area of the wearing female. The combination of the biasing of both ends toward each other, and the adjusting of the width, shape, and positioning of the U-shaped member, thereby increases the users sexual stimulation in a customizable fashion and allows the device to be easily retained in the wearer without belts or other mounting devices from the clamping action which is also enhanced.

The head portion of the device, located at the proximal end, is preferably shaped to stabilize the device by intra vaginal surface contact within the anatomic ledge formed above the pubic symphysis of the female wearing the device. The undersurface of this intra vaginal positioned head the U-shaped member is in continuous biased contact with the G-spot thereby providing direct physical stimulation thereto in a motion-energy transfer from the movement of either the wearer's hand on the device or movement of a sexual partner engaged upon the elongated member attached to the U-shaped member.

The distal end of the U-shaped member provides the user wearing the device constant physical contact and stimulation of the clitoral area with the exterior surface of the U-shaped member through the force and movement communicated from the sexual partner engaged upon the elongated member, or the wearer's hand upon the elongated member. An optional ribbed portion of the external surface, adjacent to the distal end of the U-shaped member, provides a means to increase physical stimulating of the clitoral area. Thus, the device may be employed for increased sexual stimulation by the wearer alone imparting force to the elongated member, or by a partner through the movement of each other during intercourse and the resulting transfer of force and motion to the device.

A bifurcating ridge on an inner portion of the external surface of the U-shaped member, adjacent to the proximal end, serves to provide additional physical contact with the G-spot area and is especially preferred. The ridge projects away from the center axis of the U-shaped member a distance to allow it to bury into the flesh of the user in the G-spot area slightly more than the adjacent exterior surface.

Also preferred in a mode of the device, at a point adjacent to the distal end of the U-shaped member formed by a bend of the U-shaped member, is a hooked portion. The hooked portion is a portion of the member positioned intra vaginally, which bends inward toward the distal end at an increased angle. In use, the hooked portion provides an increased contact force at the proximal end of the U-shaped member within the anatomic ledge when positioned above the pubic symphysis. This hooked contact provides means to increase the surface contact force with the G-spot while simultaneously providing a more stable clamping engagement of the device caused by the biasing of both ends toward each other.

As noted, in a preferred mode of the device an engagement point is provided adjacent to the distal end for a projecting elongated member. The elongated member can be provided in a kit form featuring a plurality of such elongated phallic shaped members of different lengths and circumferences and shaped to allow the partner of the wearer to choose one which provides optimum sexual stimulation during intercourse.

Additionally, provided in one mode of the device herein, is the inclusion of means for vibration at the proximal end of the U-shaped member to provide vibratory stimulation to the G-spot. Also preferred is means for clitoral stimulation which currently is provided by one or a combination of raised edges positioned at an engagement point along the U-shaped member, and/or, a second means for vibration at the same engagement point. This means vibration at the distal end may be provided by engagement of a vibrator as the elongated member attachable adjacent to the distal end. This is especially preferred in that using a vibrator for the projecting elongated member will impart a vibrating action to the U-shaped member upon the adjacent clitoral region of the wearer while concurrently imparting a vibrating force to the partner of the wearer during contact on or with the elongated member.

With respect to the above description, it is to be understood that the invention is not limited in its application to the details of construction and to the arrangement of the components in this specification or illustrated in the drawings. The device and method herein described, providing a retainable sexual aid for females, is capable of other embodiments and of being practiced and carried out in various ways which will be obvious to those skilled in the art upon reading this disclosure. Also, it is to be understood that the phraseology and terminology employed herein are for the purpose of description and should not be regarded as limiting.

As such, those skilled in the art will appreciate that the conception upon which this disclosure is based may readily be utilized as a basis for designing of other structures, methods and systems for carrying out the several purposes of the present disclosed self-retained female sexual aid device. It is important, therefore, that the claims and disclosure herein be regarded as including such equivalent construction and methodology insofar as they do not depart from the spirit of the present invention.

It is an object of this invention to provide a sexual aid which may be self-retained on a user without the need for straps or mounting aids.

An additional object of this invention is the provision of G-spot and clitoral stimulation to a wearing female user through a clamping pressure and motion of the phallic shaped member engaged at the distal end of the device.

A further object of this invention is the provision of a sexual aid which allows a user to be stimulated by a sexual partner engaged with and acting upon the U-shaped member during a sexual encounter with that partner.

Yet another object of this invention, is the provision of a sexual aid which provides ongoing concurrent G-spot and clitoral stimulation with both pressure and vibration.

These together with other objects and advantages which become subsequently apparent reside in the details of the construction and operation as heretofore described with reference being had to the accompanying drawings forming a part thereof, wherein like numerals refer to like parts throughout.

BRIEF DESCRIPTION OF DRAWING FIGURES

FIG. 1 shows a side view of one mode of the sexual aid device depicting the U-shaped member having an engageable projecting member adjacent to a distal end.

FIG. 2 is an overhead view of the device of FIG. 1 showing a larger body diameter of the U-shaped member at a proximal end and a projecting ridge from the exterior surface.

FIG. 5 depicts a user positionable skeletal member for coaxial engagement within the U-shaped member having bendable joints and an engagement for a projecting member.

FIG. 6 shows the ratchet or clutch formed at the bendable points along the structure of FIG. 5.

FIG. 9 depicts the device engaged with a female wearer having the proximal end in contact with the G-spot area and the distal end in contact with the clitoral area.

DETAILED DESCRIPTION OF PREFERRED EMBODIMENTS

Figure 3:
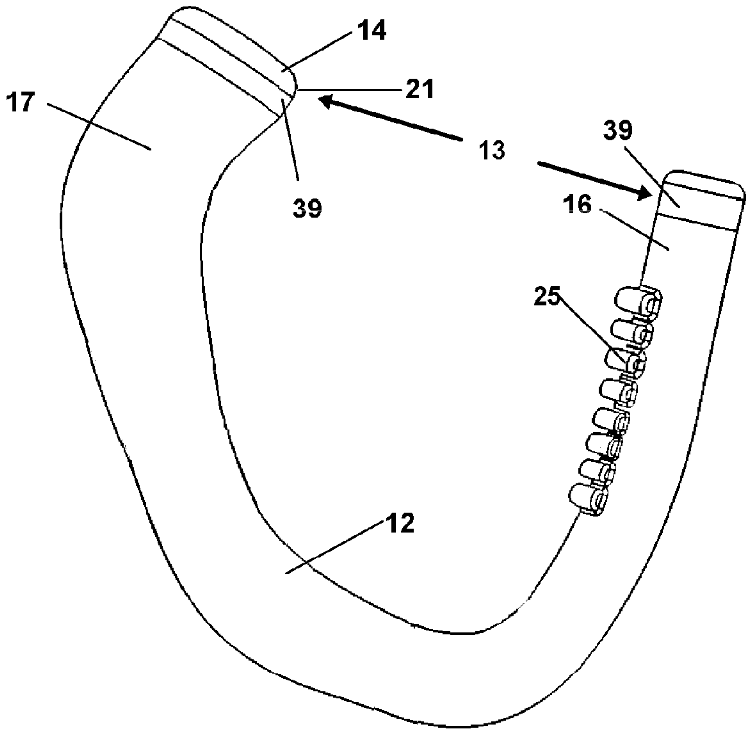
FIG. 3 depicts a mode of the device formed as a unitary structure without a projecting member at the distal end.

Referring now to the drawings of FIGS. 1-10 showing the sexual aid device 10 in various preferred modes, wherein similar parts are identified by like reference numerals which may be found in one or more of the drawings.

As shown in figures the device 10, is configured to provide a self-retained biased engagement of the device 10 with a female wearer, as shown in FIG. 9, without the aid of belts or straps but instead using a clamping action provided by a force of the ends of the device toward each other.

So employed, the device 10 has a generally U-shaped member 12 having a first or proximal end 14 which is adapted for a biased contact in an intra vaginal engagement with the wearer through a hooked portion 17 formed by a bend adjacent to the proximal end 14 of the U-shaped member 12. A projection 21 at the proximal end 14 provides increased force and friction with the G-spot area 19 of the female user as shown in FIG. 9, is preferred to increase sexual stimulation and provide a better mount of the proximal end 14 intra vaginally. The term "U-shaped" herein employed, is a general description of the shape of the member 12 and not intended in any fashion to limit the shape of the claimed device 10 which as those skilled in the art will realize could adjust to other shapes and serve the purpose intended.

Adjacent to the distal end 16 of the U-shaped member 12, opposite the proximal end 14, is located an external surface portion 35 adapted in a shape to provide enhanced frictional compressed engagement against the lower abdomen and clitoral area 23 of the female wearing the device 10. This frictional pressured engagement is provided in all modes of the U-shaped member 12. However it is particularly enhanced when a skeletal structure 18 is engaged axially within the U-shaped member 12.

Figure 4:
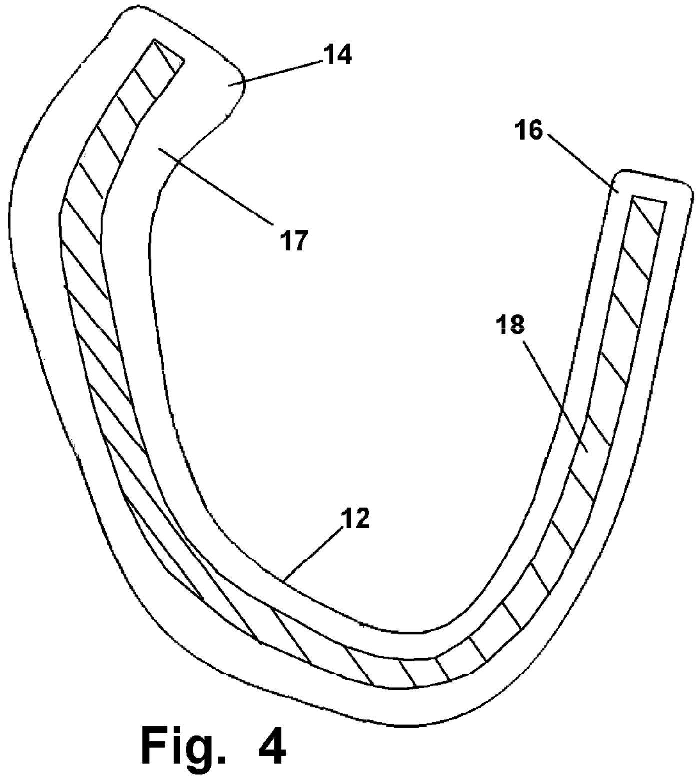
FIG. 4 shows a slice through the U-shaped member and a skeletal component running axially a distance through the U-shaped member.
Figure 7:
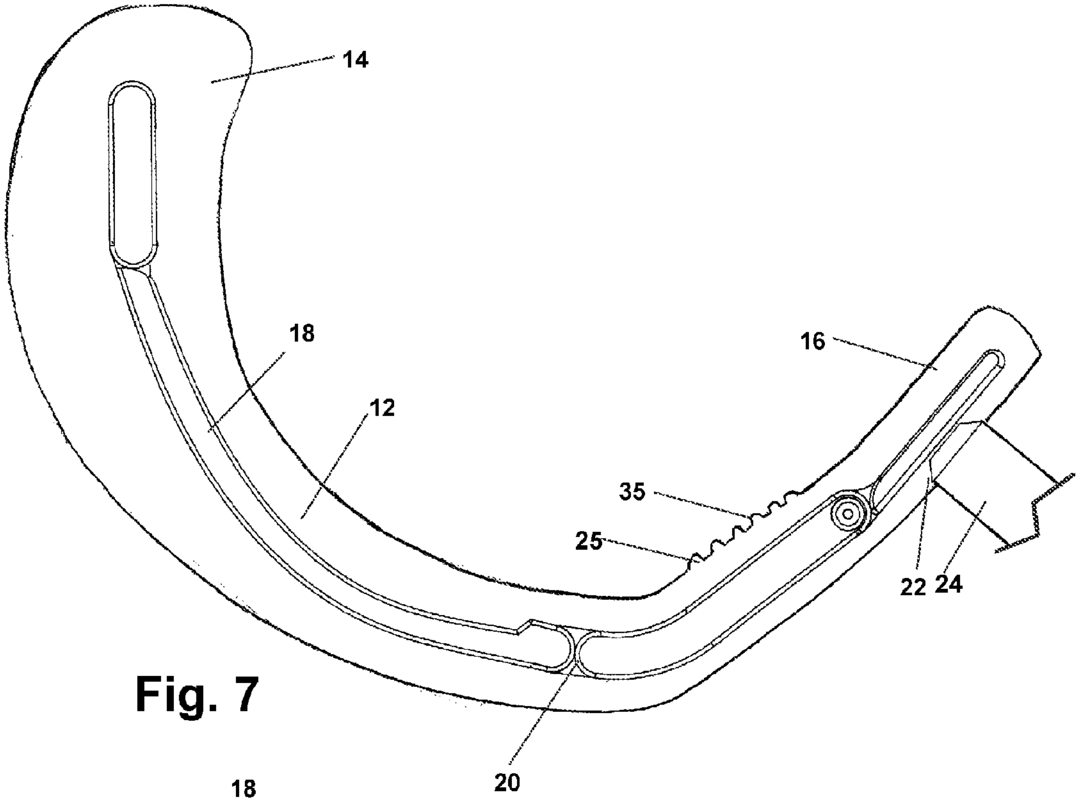
FIG. 7 shows the device of FIG. 1 having the coaxial skeletal member of FIG. 5 therein in an expanded position, and a removably engageable projecting member at the distal end.
Figure 8:
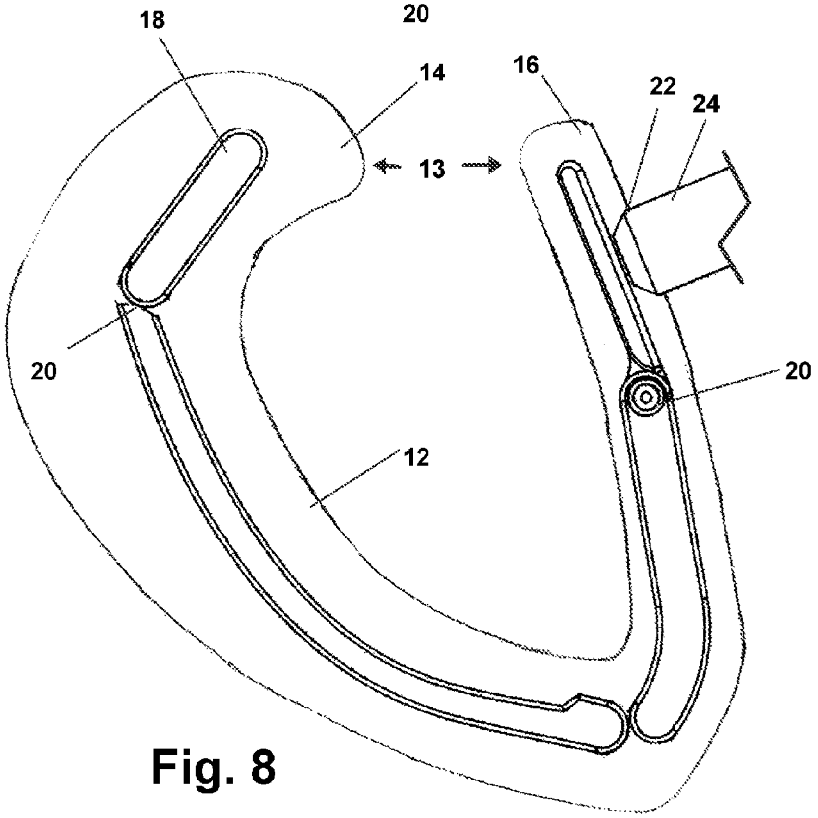
FIG. 8 depicts the device as in FIG. 7 having been moved to a compressed position by bending of bendable points of the skeletal member.

The internal skeletal structure 18 may be formed of stiffer or higher durometer resilient plastic or silicon material, or by spring steel, fiberglass, or a material which is sufficiently resilient to provide an increased biasing proximal end 14 toward the distal end 16 once pulled apart from their static or original position as in FIGS. 3-4. The increase in distance between the proximal end 14 and distal end 16 occurs during engagement of the device in a wearer as in FIG. 9 where the body tissues serve to pull the two ends away, and the biasing force of the material forming the U-shaped member 12, or as enhanced by an included vibrator.

As noted, this biasing force is a most important aspect of the device 10 to provide for the self-retention, and an adjustable mechanical communication for motion transfer between the U-shaped member 12 and an elongated member 24 projecting from, and engaged with a co-operatively engageable engagement point 22 adjacent to the distal end 16 of the U-shaped member 12.

The elongated member 24 so engaged provides a user in a solo employment of the device 10, a handle of sorts to grip and impart their hand force to move the elongated member 24 and the engaged U-shaped member 12 in various different directions. This movement provides a means to increase intra vaginal and external stimulation of the wearer's erogenous zones.

When the device 10 is employed between two parties, the elongated member 24 extending from the user-engaged U-shaped member 12, may be employed to stimulate external erogenous areas of the partner and/or to penetrate the wearer's sexual partner and provide intra vaginal sexual stimulation. This stimulation is enhanced by movement of the wearer and partner and resulting force imparted to the U-shaped member 12 by the elongated member 24 during such moments in a joint use.

When the elongated member 24 is engaged with the sexual partner, or used by the wearer's hand, the forces imparted to the U-shaped member 12 thereby provide direct physical contact and stimulation of the exterior of the proximal end 14 with the G-spot area adjacent to proximal end 14, and to the clitoral area 23 in contact with the distal end 16.

The skeletal structure 18 if malleable, provides a means to adjust the gap 13 or space between the distal end 16 and proximal end 14 in the neutral position, as formed and not engaged with the wearer. Since making the gap smaller increases the biasing force and making it larger decreases that force, the adjusting of the shape of the U-shaped member 12 using the skeletal structure 18 provides a means to increase or decrease the biasing force toward the two ends, and the pressured engagement upon the ledge 19 above the pubic symphysis adjacent to the G-spot 15, and on the abdomen and clitoral area 23. For a malleable or configurable skeletal structure 18 a simple soft metal rod might be employed such as aluminum which may be bent and thus bend the shape of the U-shaped member 12. In a mode of the device 10 with increased utility, one or preferably a plurality of malleable or adjustable points 20 are positioned along the coaxially positioned skeletal structure 18 as in FIGS. 5-6. This allows the user to adjust the position of the proximal end 14 to achieve maximum stability and the most pleasurable sensations against the G-spot 15. It also allows the user to adjust the distance between the proximal and distal ends to vary the bias toward each other and achieve a compressed engagement of the ends 14 and 16 against the abdomen and G-spot 15 to hold the device 10 self retained. It further allows the user a means for adjustable pressure over the clitoral area 21.

To provide for concurrent external stimulation or penetration of a second user concurrently with the wearer, the engagement point 22 is provided to engage an elongated member 24 projecting from the U-shaped member 12. A conventional threaded or frictional engagement of a first end of the elongated member 24 with the U-shaped member 12 and or any skeletal component 18 may be employed. The elongated member 24 can be provided in a kit form, featuring a plurality of different elongated members 24 of different lengths, and different circumferences or shapes, to allow the partner of the wearer to choose one which provides optimum sexual stimulation during intercourse.

Particularly preferred in all modes of the device 10 is a means for clitoral area 23 stimulation which currently is provided by one or a combination of ridges 25 positioned at a clitoral stimulation point adjacent to the distal end 16 along the U-shaped member 12.

Further, in a particularly preferred mode of the device 10, at the proximal end 14 along the hooked portion 21 is a projection 21 forming a projection 21 and curved undersurface of the device 10 at the proximal end 14. This is most important in that it serves to provide a stable mount for the device 10 with the curved undersurface of the hooked portion 17 and with the projection 21 resting upon the ledge over the pubic bone 31. This serves to sandwich the G-spot 15 between the device 10 and the pubic bone 31 and to maintain the device 10 in a stable position on the user without belts or other exterior supports as the projection 21 is supported by the underlying pubic bone 31 stops excessive rotation of the device 10 and helps maintain the distal end 16 in a correct position outside the body of the wearer. This engagement means has been found to be especially stable without the need for belts or straps to hold the device 10 during use with two people, and to also provide constant contact of the area adjacent to the proximal end 14 with the G-spot 15 for intense and constant stimulation to the user simulating transfer of motion energy from the phallic shaped elongated member engaged with the sexual partner.

In one preferred mode of the device 10 herein, optionally a means for vibration 39 at the proximal end 14 of the U-shaped member 12 may be provided to provide direct vibratory stimulation to the G-spot 15 in biased engagement with the proximal end 14. Such vibration would be in addition to the pressure and movement provided by the direct energy transfer from movement of the sexual partner upon the elongated member 24 projecting extension.

Additionally, and particularly preferred, the elongated member 24 engaged adjacent to the distal end 16 of the device 10 may be a vibrator. So configured, the elongated member 24 would communicate vibration to the U-shaped member 12 and stimulating spots on the wearer, and also provide intense physical stimulation to a partner with whom the vibrating elongated member 24 would be in contact.

Figure 10:
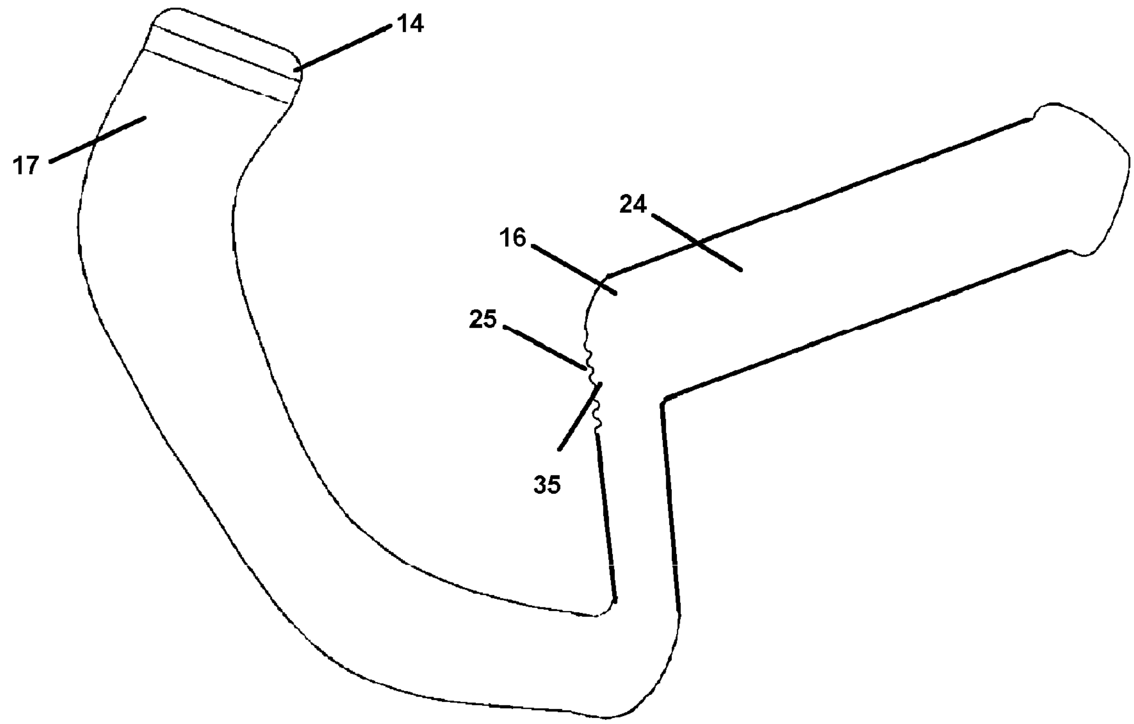
FIG. 10 shows the simplest mode of the disclosed device wherein the elongated member extends from the distal end of the U-shaped member in a unitary structure.

While the most preferred modes of the device 10 show the elongated member 24 being engageable to the distal end 16 of the U-shaped member 12, the device 10 can be formed in a unitary structure in a once-piece mode as shown in FIG. 10. This would be the simplest mode of the disclosed device 10 and would still provide the biased inward force of the two ends of the U-shaped member 12 to achieve the engagement with a user. However it may be formed of a single piece of silicone or with a skeletal component 18 running axially through the U-shaped member 12 and optionally through the axis of the elongated member 24. This mode while simple in construction still provides a huge leap in performance and function to users from conventional sexual aids offering no biased engagement with a user nor provision of an elongated member 24 to transfer motion forces to the wearer from the partner and vice versa.

While all of the fundamental characteristics and features of the sexual aid system herein have been shown and described, with reference to particular embodiments thereof, a latitude of modification, various changes and substitutions are intended in the foregoing disclosure and it will be apparent that in some instances, some features of the invention may be employed without a corresponding use of other features without departing from the scope of the invention as set forth. It should also be understood that various substitutions, modifications, and variations may be made by those skilled in the art without departing from the spirit or scope of the invention. Consequently, all such modifications and variations and substitutions are included within the scope of the invention as defined by the following claims.

What is claimed is:

1. A sexual aid apparatus, comprising:

A substantially U-shaped, member having a proximal end and distal end; and said proximal end positioned to oppose said distal end at a distance therefrom, said distance defined by a gap;

said proximal end and said distal end of said U-shaped member resisting movement away from each other to positions wider than said gap;

said proximal and distal ends adapted to form a biased engagement with a body of a user;

a skeletal member running axially within said U-shaped member;

said skeletal component providing means to adjust a force of said biased engagement to said body of said user; and whereby said sexual aid is engageable to said body of said user by said force of said biased engagement of said proximal end against an internal structure of the body of said user, and said biased engagement of said distal end against an exterior surface of said body of said user, when said U-shaped member is positioned in an as-used position with said internal structure and said exterior surface within said gap.

2. The sexual aid apparatus of claim 1 additionally comprising:

said skeletal member formed of materials from a group of materials including aluminum, stainless steel, fiberglass, and resilient plastic material having a durometer higher than that of said member.

3. The sexual aid apparatus of claim 2 additionally comprising:

a substantially hook shaped undersurface adjacent to said proximal end; and said undersurface providing means to support said proximal end upon an underlying ledge over a pubic bone of said user when said U-shaped member is in said as-used position.

4. The sexual aid apparatus of claim 1 additionally comprising:

said skeletal member formed of malleable material bendable to provide a means to reshape said U-shaped member.

5. The sexual aid apparatus of claim 4 additionally comprising:

a substantially hook shaped undersurface adjacent to said proximal end; and said undersurface providing means to support said proximal end upon an underlying ledge over a pubic bone of said user when said U-shaped member is in said as-used position.

6. The sexual aid apparatus of claim 5 additionally comprising:

an elongated member extending from an engagement to said U-shaped member adjacent to said distal end; and said elongated member engageable with a hand of said user, or the body of a second user to impart a force to said U-shaped member; and said force communicated through said U-shaped member to one or both of, said internal structure and said external surface, whereby said sexual aid in said as-used position is employable by said first user alone through a hand contact by said first user with said elongated member, and said sexual aid is shareable in said as-used position with said second user through internal and external contacts with a body of said second user, said internal and external contacts providing means to generate said force.

7. The sexual aid apparatus of claim 6 additionally comprising:

said internal structure being the G-spot of said first user and said external surface being the clitoral area of said first user.

8. The sexual aid apparatus of claim 4 additionally comprising:

an elongated member extending from an engagement to said U-shaped member adjacent to said distal end; and said elongated member engageable with a hand of said user, or the body of a second user to impart a force to said U-shaped member; and said force communicated through said U-shaped member to one or both of, said internal structure and said external surface, whereby said sexual aid in said as-used position is employable by said first user alone through a hand contact by said first user with said elongated member, and said sexual aid is shareable in said as-used position with said second user through internal and external contacts with a body of said second user, said internal and external contacts providing means to generate said force.

9. The sexual aid apparatus of claim 8 additionally comprising: said internal structure being the G-spot of said first user and said external surface being the clitoral area of said first user.

10. The sexual aid apparatus of claim 9 additionally comprising:

means for vibration engaged with said elongated member, said means for vibration communicating a vibration through said elongated member and said U-shaped member to said G-spot and said clitoral area.

11. The sexual aid apparatus of claim 1 additionally comprising:

a substantially hook shaped undersurface adjacent to said proximal end; and said undersurface providing means to support said proximal end upon an underlying ledge over a pubic bone of said user when said U-shaped member is in said as-used position.

12. The sexual aid apparatus of claim 1 additionally comprising:

an elongated member extending from an engagement to said U-shaped member adjacent to said distal end; and said elongated member engageable with a hand of said user, or the body of a second user to impart a force to said U-shaped member; and said force communicated through said U-shaped member to one or both of, said internal structure and said external surface, whereby said sexual aid in said as-used position is employable by said first user alone through a hand contact by said first user with said elongated member, and said sexual aid is shareable in said as-used position with said second user through internal and external contacts with a body of said second user, said internal and external contacts providing means to generate said force.

13. The sexual aid apparatus of claim 12 additionally comprising:

said internal structure being the G-spot of said first user and said external surface being the clitoral area of said first user.

14. The sexual aid apparatus of claim 13 additionally comprising:

means for vibration engaged with said elongated member, said means for vibration communicating a vibration through said elongated member and said U-shaped member to said G-spot and said clitoral area.

15. The sexual aid apparatus of claim 12 additionally comprising:

said engagement of said elongated member being a removable engagement;

said elongated member being a member of a plurality of said elongated members in a kit, each of said plurality having differing exterior dimensions from the remaining of said plurality; and said elongated member being selectable from said kit by said first user or said second user to provide a said elongated member having said exterior dimensions which best adapted said internal or external contact with said second user to maximize a sexual stimulation of said second user.

* * * * *